United States Patent [19]

Cardis

[11] Patent Number: 5,200,099
[45] Date of Patent: Apr. 6, 1993

[54] REACTION PRODUCTS OF DIALKYL AND TRIALKYL PROSPHITES WITH ELEMENTAL SULFUR AND THEIR USE IN LUBRICANT COMPOSITIONS

[75] Inventor: Angeline B. Cardis, Florence, N.J.

[73] Assignee: Mobil Oil Corporation, Fairfax, Va.

[21] Appl. No.: 461,201

[22] Filed: Jan. 5, 1990

Related U.S. Application Data

[63] Continuation-in-part of Ser. No. 108,599, Oct. 15, 1987, abandoned, which is a continuation-in-part of Ser. No. 883,665, Jul. 9, 1986, Pat. No. 4,717,491.

[51] Int. Cl.$^5$ ............................................. C10M 137/04
[52] U.S. Cl. .............................. 252/32.7 E; 252/46.7; 558/123
[58] Field of Search ......................... 252/32.7 E, 46.7; 558/123

[56] References Cited

U.S. PATENT DOCUMENTS

| | | | |
|---|---|---|---|
| 2,647,140 | 7/1953 | Jones | 558/123 |
| 3,020,306 | 2/1962 | Birum | 558/123 |
| 3,080,274 | 3/1963 | Legator | 558/123 |
| 4,431,552 | 2/1984 | Salentine | 252/32.7 E |

OTHER PUBLICATIONS

G. M. Kosolapoff & L. Maier, Organic Phosphorus Compounds, 532–533; Feb. 11, 1976.

*Primary Examiner*—Jacqueline Howard
*Attorney, Agent, or Firm*—Alexander J. McKillop; Malcolm D. Keen; Jessica M. Sinnott

[57] ABSTRACT

Dialky and trialky phosphites are reacted with sulfur. The resulting product is the desired lubricant additive which is mixed with suitable lubricating oils.

2 Claims, No Drawings

REACTION PRODUCTS OF DIALKYL AND TRIALKYL PROSPHITES WITH ELEMENTAL SULFUR AND THEIR USE IN LUBRICANT COMPOSITIONS

This is a contination-in-part application of copending U.S. application Ser. No. 108,599 filed Oct. 15, 1987 which is a continuation-in-part of U.S. application Ser. No. 883,665 filed Jul. 9, 1986, now U.S. Pat. No. 4,717,491 which are incorporated herein by reference.

NATURE OF THE INVENTION

This invention relates to reaction products of dialkyl and trialkyl phosphites with elemental sulfur, and use of these products in lubricating oil formulations.

PRIOR ART

U.S. Pat. No. 3,984,448 discloses the use of metal oxides, such as those of copper, calcium, barium, magnesium, zinc, cadmium, titanium or lead in conjunction with elemental sulfur and O,O-dialkylphosphorus acid esters to produce dialkyl thiophosphates.

Although dithiophosphate products are known lubricant additives, their preparation involves processes resulting in noxious, undesirable by-products such as hydrogen sulfide and chloride-containing waste streams. Accordingly a primary object of this invention is to provide a process for preparing thiophosphate products which eliminates the production of the aforementioned undesirable by-products.

SUMMARY OF THE INVENTION

In brief, this invention comprises in one aspect reacting dialkyl or trialkyl phosphites with elemental sulfur to obtain a desired lube oil additive. This invention also comprises a method for preparing lube oils wherein the aforedescribed additives are added to a selected lubricating oil. This invention further comprises the resulting lube oil product.

DESCRIPTION OF THE INVENTION

In the present invention the lube oil additive is obtained by reacting dialkyl or trialkyl phosphites of the general formula

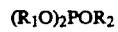

$(R_1O)_2POR_2$ where $R_1$ is a hydrocarbon radical of 4 to 18 carbon atoms and $R_2$ is hydrogen or a hydrocarbon radical of 4 to 18 carbon atoms with elemental sulfur in the absence of any added catalyst in the presence of pulverulent sulfur at elevated temperature. Useful dialkyl or trialkyl phosphites include oleyl, 2-ethyl hexyl, 1,3-dimethylbutyl, tridecyl, isodecyl, octyl and butyl, and mixed phosphites of the above radicals. If desirable, an unreactive organic solvent can be utilized. Preferably the organic solvent is selected from benzene, toluene, xylene, and mixed alkyl and aromatic petroleum distillates.

The pulverulent sulfur should conveniently have a mean particle size of less than one millimeter, preferably less than 0.01 millimeters, as this enables the reaction to be shortened. Reaction temperatures between 75° C. and 110° C. are preferred and a mole ratio of sulfur to phosphite of 0.8 to 1.2 is preferred. The reaction is carried out, preferably under a blanket of material such as nitrogen or other non-reactive gas. At the end of the reaction period the reaction mixture is allowed to cool to room temperature. The desired product is then stripped under vacuum to remove solvent and volatile byproducts and can be subsequently filtered or decanted from the reaction vessel.

The additive products of this invention are used with lubricating oils or greases to the extent of from about 0.1% to about 10% by weight of the total composition. Furthermore, other additives, such as detergents, antioxidants, antiwear agents and the like may be present. These can include phenates, sulfonates, succinimides, zinc dialkyl dithiophosphates, polymers, calcium and magnesium salts of phenates and sulfonates, including overbased salts of the same, and the like.

The lubricants contemplated for use with the esters herein disclosed include mineral and synthetic hydrocarbon oils of lubricating viscosity, mixtures of mineral oils and synthetic oils and greases from any of these, including the mixtures. The synthetic hydrocarbon oils include long-chain alkanes such as cetanes and olefin polymers such as oligomers of hexene, octene, decene, and dodecene, etc. These thiophosphate esters are especially effective in synthetic oils formulated using mixtures of synthetic hydrocarbon olefin oligomers and lesser amounts of hydrocarbyl carboxylate ester fluids. The other synthetic oils, which can be used alone with the borated compounds of this invention, or which can be mixed with a mineral or synthetic hydrocarbon oil, include (1) fully esterified ester oils, with no free hydroxyls, such as pentaerythritol esters of monocarboxylic acids having 2 to 20 carbon atoms, trimethylolpropane esters of monocarboxylic acids having 2 to 20 carbon atoms, (2) polyacetals and (3) siloxane fluids. Especially useful among the synthetic esters are those made from polycarboxylic acids and monohydric alcohols. More preferred are the ester fluids made by fully esterifying pentaerythritol, or mixtures thereof with di- and tripentaerythritol, with an aliphatic monocarboxylic acid containing from 1 to 20 carbon atoms, or mixtures of such acids.

A wide variety of thickening agents can be used in the greases of this invention. Included among the thickening agents are alkali and alkaline earth metal soaps of fatty acids and fatty materials having from about 12 to about 30 carbon atoms per molecule. The metals are typified by sodium, lithium, calcium and barium. Fatty materials are illustrated by stearic acid, hydroxystearic acid, stearin, cottonseed oil acids, oleic acid, palmitic acid, myristic acid and hydrogenated fish oils.

Other thickening agents include salt and salt-soap complexes as calcium stearate-acetate (U.S. Pat. No. 2,197,263), barium stearate acetate (U.S. Pat. No. 2,564,561), calcium stearate-caprylate-acetate complexes (U.S. Pat. No. 2,999,065), calcium caprylate-acetate (U.S. Pat. No. 2,999,066), and calcium salts and soaps of low-, intermediateand high-molecular weight acids and of nut oil acids.

Another group of thickening agents comprises substituted ureas, phthalocyanines, indanthrene, pigments such as perylimides, pyromellitdiimides, and ammeline.

The preferred thickening gelling agents employed in the grease compositions are essentially hydrophobic clays. Such thickening agents can be prepared from clays which are initially hydrophilic in character, but which have been converted into a hydrophobic condition by the introduction of long chain hydrocarbon radicals onto the surface of the clay particles prior to their use as a component of a grease composition, as, for example, by being subjected to a preliminary treatment with an organic cationic surface active agent, such as an onium compound. Typical onium compounds are tetraalkylammonium chlorides, such as dimethyl dioctadecyl ammonium chloride, dimethyl dibenzyl ammonium chloride and mixtures thereof. This method of conversion, being well known to those skilled in the art, is believed to require no further discussion, and does not form a part of the present invention. More specifically, the clays which are useful as starting materials in forming the thickening agents to be employed in the grease compositions, can comprise the naturally occurring chemically unmodified clays. These clays are crystalline complex silicates, the exact composition of which is not subject to precise description, since they vary widely from one natural source to another. These clays can be described as complex inorganic silicates such as aluminum silicates, magnesium silicates, barium silicates, and the like, containing, in addition to the silicate lattice, varying amounts of cation-exchangeable groups such as sodium. Hydrophilic clays which are particularly useful for conversion to desired thickening agents include montmorillonite clays, such as bentonite, attapulgite, hectorite, illite, saponite, sepiolite, biotite, vermiculite, zeolite clays, and the like. The thickening agent is employed in an amount from about 0.5 to about 30, and preferably from 3 percent to 15 percent by weight of the total grease composition.

Having described the invention in general aspects, the following examples are offered as specific illustrations. Parts are by weight.

EXAMPLES

Example 1

A one-liter flask was charged with 209.3 grams of tris-2-ethylhexylphosphite and 16 grams of sulfur under a nitrogen atmosphere. The initial reaction elevated the temperature to 109° C. When the temperature started to decline, heat was applied to maintain 100° C. for eight hours. The product when analyzed was determined to contain 6.7 percent of phosphorus and 7.5 percent of sulfur.

Example 2

In accordance with the procedure of Example 1 a product was made from 208 grams of tri-isopropyl phosphite and 32 grams of sulfur. Analysis of the product showed 6.57 percent of phosphorus and 11.6 percent of sulfur.

Example 3

To 388 g (2.0 moles) dibutylhydrogen phosphite was added 64 g (2.0 moles) sulfur. The temperature was raised to 100° C. under a nitrogen atmosphere with stirring and held for eight hours. The resulting reaction mixture was cooled to ambient temperature and the desired reaction product was recovered.

Example 4

Sulfur (32 g, 1.0 mole) and bis-(2-ethylhexyl) hydrogen phosphite (306 g, 1.0 mole) were stirred under nitrogen as the temperature was increased from ambient to 100° C. Products were also made following the procedure of Example 4, from di-oleylhydrogen phosphite, and dilaurylhydrogen phosphite.

Evaluation of Products

The products described in Examples 1 and 2 were blended in mineral oil and tested in the Shell Four-Ball Wear Test. The results in Table 1 demonstrate the antiwear protection afforded by these products.

TABLE 1

| FOUR BALL WEAR TEST SCAR DIAMETER (mm) ½ Inch Balls, 52100 Steel, 60 Kg., 30 Minutes, 1.5% Additive | | | | |
|---|---|---|---|---|
| | 1000 RPM | | 2000 RPM | |
| Temperature, °F. | 200° F. | 300° F. | 200° F. | 300° F. |
| Base Stock | 1.02 | 1.92 | 4.12 | 3.85 |
| Example 1 | 0.57 | 0.75 | 0.82 | 0.87 |
| Example 2 | 0.65 | 0.50 | 0.70 | 0.70 |

The product of Example 1 was combined at 0.6 weight percent into a fully formulated hydraulic oil and compared to the same formulation using 0.7 weight percent of commercial zinc dithiophosphate in the Vickers V104C pump Wear Test (ASTM D2882) The results were as follows and demonstrated the antiwear performance of the products herein disclosed.

TABLE 2

| Formulation Containing | ASTM D28882 Wear, Milligrams |
|---|---|
| Zinc dithiophosphate | 27 |
| Example 1 Product | 22 |

What is claimed is:
1. A process for making a lubricating oil comprising:
   (a) reacting a dialkyl or trialkyl phosphite having the structural formula $(R'O)_2POR^2$ where $R'$ is an alkyl hydrocarbon radical of 4 to 18 carbon atoms and $R^2$ is hydrogen or an alkyl hydrocarbon radical of 4 to 18 carbon atoms with a reactant consisting essentially of elemental sulfur in a mole ratio of sulfur to phosphite of about 0.8 to about 1.2, at a temperature between 75° C. and about 110° C. in the absence of any catalytic material added to promote reaction of the two reactants;
   (b) separating the reaction product thereby obtained; and
   (c) blending the reaction product with a lubricating oil.
2. The process of claim 1 wherein the dialkyl or trialkyl phosphite is selected from the group consisting of oleyl, 2-ethyl hexyl, 1,3-dimethyl butyl, tridecyl, isodecyl, octyl, butyl, and mixed phosphites.

* * * * *